(12) United States Patent
Schaefer et al.

(10) Patent No.: US 7,690,067 B2
(45) Date of Patent: Apr. 6, 2010

(54) BRUSH ATTACHMENT FOR AN ELECTRIC TOOTHBRUSH

(75) Inventors: Norbert Schaefer, Frankfurt (DE); Erik Eisenkolb, Frankfurt am Main (DE); Reiner Engelmohr, Morfelden-Walldorf (DE); Hansjörg Reick, Steinbach (DE)

(73) Assignee: Braun GmbH, Kronberg (DE)

( * ) Notice: Subject to any disclaimer, the term of this patent is extended or adjusted under 35 U.S.C. 154(b) by 1162 days.

(21) Appl. No.: 10/984,570

(22) Filed: Nov. 9, 2004

(65) Prior Publication Data
US 2005/0108838 A1 May 26, 2005

(30) Foreign Application Priority Data
Nov. 13, 2003 (DE) ................. 103 52 993

(51) Int. Cl.
*A61C 17/22* (2006.01)
*A46B 13/02* (2006.01)
(52) U.S. Cl. ........................ 15/22.1; 15/176.6
(58) Field of Classification Search .................. 15/22.1, 15/176.1, 176.6
See application file for complete search history.

(56) References Cited

U.S. PATENT DOCUMENTS

| | | | |
|---|---|---|---|
| 3,369,265 A | 2/1968 | Halberstadt et al. | |
| 5,289,604 A | 3/1994 | Kressner | |
| 5,359,747 A | 11/1994 | Amakasu | |
| 5,412,827 A | 5/1995 | Müller et al. | |
| 5,836,030 A | 11/1998 | Hazeu et al. | |
| 6,308,359 B2 * | 10/2001 | Fritsch et al. | 15/22.1 |
| 6,588,042 B2 | 7/2003 | Fritsch et al. | |
| 2003/0101526 A1 | 6/2003 | Hilscher et al. | |
| 2003/0208863 A1 | 11/2003 | Green | |
| 2005/0198753 A1 * | 9/2005 | Berde et al. | 15/22.1 |

FOREIGN PATENT DOCUMENTS

| | | |
|---|---|---|
| CH | 368780 | 6/1963 |
| DE | 3129435 | 2/1983 |
| DE | 29616907 | 1/1997 |
| DE | 19745551 | 6/1998 |
| DE | 19927297 | 6/2000 |
| DE | 29823799 | 9/2000 |
| DE | 29919053 | 1/2001 |
| DE | 10112601 | 9/2002 |
| DE | 69619802 | 11/2002 |
| DE | 10159395 | 6/2003 |
| JP | 53-21650 | 2/1978 |
| WO | WO99/20202 | 4/1999 |
| WO | WO00/76420 | 12/2000 |

* cited by examiner

*Primary Examiner*—Randall Chin
(74) *Attorney, Agent, or Firm*—Fish & Richardson P.C.

(57) ABSTRACT

The invention is directed to a brush attachment adapted to be attached to and detached from a shaft of a handle of an electric toothbrush, including a bristle area, a brush shank and a plug-on part disposed in the brush shank, wherein the plug-on part includes a first spring element and a second spring element which act on the shaft when the brush attachment is plugged onto the shaft. This establishes a connection without play between the brush attachment and the shaft, enabling relatively high vibration frequencies to be transmitted.

52 Claims, 5 Drawing Sheets

BRUSH ATTACHMENT FOR AN ELECTRIC TOOTHBRUSH

CROSS-REFERENCE TO RELATED APPLICATIONS

This application claims priority to German Patent Application No. DE 103 52 993 4, filed on Nov. 13, 2003, which is incorporated herein by reference in its entirety.

TECHNICAL FIELD

This disclosure relates to electric toothbrushes and attachments therefor.

BACKGROUND

A replaceable brush attachment for an electric toothbrush is known from U.S. Pat. No. 3,369,265. On the brush attachment are bristles in a fixed arrangement. The end of the brush attachment intended for connecting to the handle has a cavity in which provision is made for two opposite lying detent notches, both of which are arranged in the same axial position. A connecting pin of a handle equipped with corresponding detent elevations engages in these detent notches. The end of the brush attachment intended for connecting to the handle is divided by two slots into two legs which are spread apart when the brush attachment is plugged onto the connecting pin, thus permitting a snap-action effect. The end of the connecting pin engages in the end of the cavity, which is conformably shaped in flush fashion.

WO 00 76420 describes an electric toothbrush with a brush attachment. The latter has a coupling means formed by a rubbery component with a sawtooth serration, which frictionally engages over an extension of the housing. A clamping ring is used to achieve high retaining forces without making it difficult to push on the brush attachment. This ring is rotatably held on the brush attachment and equipped with a run-on ramp that grips the housing extension. In addition, provision is made for an anti-rotation device using a coupling sleeve. This solution is relatively elaborate in its construction and hence expensive.

A brush attachment of the prior-art type is known from WO 99 20202. The brush attachment can be plugged onto a handle of an electric toothbrush that has a receiving socket from which a shaft projects. An axial securing element arranged in a brush shank of the brush attachment has a first spring element that is configured like a detent finger and engageable in a groove of the shaft. A second spring element in the form of a bending bar acts on the receiving socket on the handle and is part of a sleeve inserted in the brush shank. This plug-on mechanism is intended for a brush attachment on which a bristle carrier mounted on the brush shank is to be set in oscillatory rotational motion by the shaft of the handle.

It is an object of the present invention to construct a brush attachment of the prior-art type such that it can also be used on a toothbrush with which dental cleaning is supported by a fast vibratory motion of the bristles. The transmission of these vibrations from the handle to the brush attachment should take place without clattering noises in the attachment area, and it should still be easy to plug on and remove the brush attachment. The plug-on mechanism should also display these advantageous characteristics at comparatively high vibration frequencies of preferably 100 to 300 Hz.

This object of the invention is accomplished in that the brush attachment has a plug-on part on which a first and a second spring element are arranged in an axially offset relation to each other and which act on the shaft when the brush attachment is plugged onto the shaft.

This solution enables a connection without play between the shaft and the brush attachment, whereby relatively high forces and torques can be transmitted. The brush attachment is supported on the shaft under bias by in particular elastic shaped elements.

In an advantageous further configuration of the brush attachment of the invention the first and the second spring element are arranged in the same radial position. As a result, the pressure forces of the spring elements act in the same plane, or to be more exact in the same radial direction. This is advantageous with regard to the behavior of the brush attachment when plugged onto the shaft.

According to an advantageous embodiment, provision is made for the first spring element to be constructed as a detent finger that extends axially and engages in an approximately V-shaped detent groove of the shaft. This arrangement can be implemented at very little cost and tells the user of the brush attachment by means of an audible and tangible snap action that the brush attachment is securely seated on the handle.

When, in accordance with an advantageous arrangement, the second spring element is arranged on an area close to the bristle carrier while the first spring element is arranged at a location more remote from the bristles, the second spring element can then act on the free end of the shaft. This means that only the first spring element acts at the beginning of the plug-on operation and very little resistance can be felt when plugging on. The second spring element, which is preferably calculated to have a higher pressure force, does not come into play until at the end.

A preferred arrangement of the detent finger wherein the finger points in the direction of the handle, has the advantage of allowing the detent groove to be deeper and bigger, as the shaft generally has a larger diameter in the vicinity of the handle. The bigger detent groove and the bigger detent finger enable a better snap action to be provided.

A preferred embodiment of the brush attachment of the invention wherein the second spring element is an axially aligned spring bar with a bend curved in the direction of the shaft, whereby the spring bar is arranged between two axial slots of the plug-on part, has the advantage of being an economical and durable solution. A necessary pressure force is assured even after very frequent changing of the brush attachment.

An even better hold is afforded by a third spring element in accordance with another advantageous configuration of the brush attachment of the invention. The third spring element is arranged in an axially offset position relative to the first two spring elements. Conveniently, the plug-on part has several, in particular three, radially offset resilient fingers that urge against the shaft in the mounted state. Through this supporting of the shaft at least three axially offset points the brush attachment is seated particularly quietly and securely on the shaft. The radial support of the plug-on part is also effected preferably at three points of the shaft.

According to another preferred embodiment of the brush attachment of the invention, provision is made for the brush attachment to be constructed for mounting on a shaft having several cross sectional areas, the shaft having an essentially D-shaped cross section at its forward end close to the bristle carrier and a circular cross section at its rear end close to the handle, the forward end of the shaft preferably having a flattening against which a spring element rests. This enables user-friendly attachment and good guidance of the brush attachment. On the one hand, the shaft tip has a small cross section that is inserted in a relatively large receiving opening of the plug-on part. On the other hand, the brush attachment with its bristles has the correct radial alignment. In the first moment of the plug-on movement it is even possible for the bristles to be in any radial alignment. Using a practically automatic rotary movement of the brush attachment in an already partly inserted position, a precise alignment of the bristles is achieved by means of insertion bevels and/or curves running preferably transverse to the shaft on the shaft and/or the plug-on part. The plugging on operation is thus greatly facilitated. Incorrect plugging on is impossible.

When the plug-on part is constructed for mounting on a shaft having at least two circular cross sectional areas of various diameters, with different spring elements resting against the different cross sectional areas, then it is possible for third spring elements, for example, to rest against an enlarged cross sectional area. Preferably provision is made for a first diameter for the first spring element and for a second, bigger diameter for the third spring element. When the brush attachment is pushed on, very little force is required initially because the third spring element does not take support upon the shaft until at the end of the push-on movement. This makes it easy to insert the plug-on part.

It is an advantage for the brush attachment to be encompassed by a soft-elastic padding that extends over at least a section of the brush attachment in order to equip the brush attachment with a shock-absorber function. This padding is preferably arranged in a region proximate the bristles, with a soft-elastic component preferably encompassing a hard part at least in a region opposite the bristles. This shock absorber function enables the forces acting on the teeth on contact with the bristle carrier at high frequencies of vibration to be dampened and reduced. As the result, the user does not experience the contact as bothersome or indeed painful. Drive frequencies can lie above 100 Hz and particularly between 200 and 500 Hz, for example 260 Hz or higher. Without a suitable shock absorbing effect the high acceleration could cause damage to the teeth in extreme cases. It suffices for the padding to extend over a partial area, preferably about half of a circumference and/or only in the vicinity of the brush attachment. In particular, a soft-elastic component additionally covers side areas of the brush attachment in full or in part. The padding can have a structured, in particular studded or ribbed, surface. It is optimal for the soft-elastic component to have a Shore hardness of 30 to 60 A Shore.

An embodiment of a brush attachment of the invention, the present invention itself as well as further advantages thereof will be explained in the following with reference to the description of the accompanying drawing.

DESCRIPTION OF DRAWINGS

In the Figures, like parts are assigned like reference characters.

DETAILED DESCRIPTION

Figure 1:
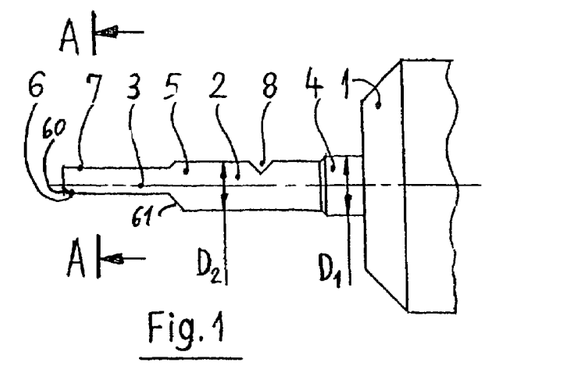
FIG. 1 is a side view of a section of a handle of an electric toothbrush, showing a shaft.
Figure 3:
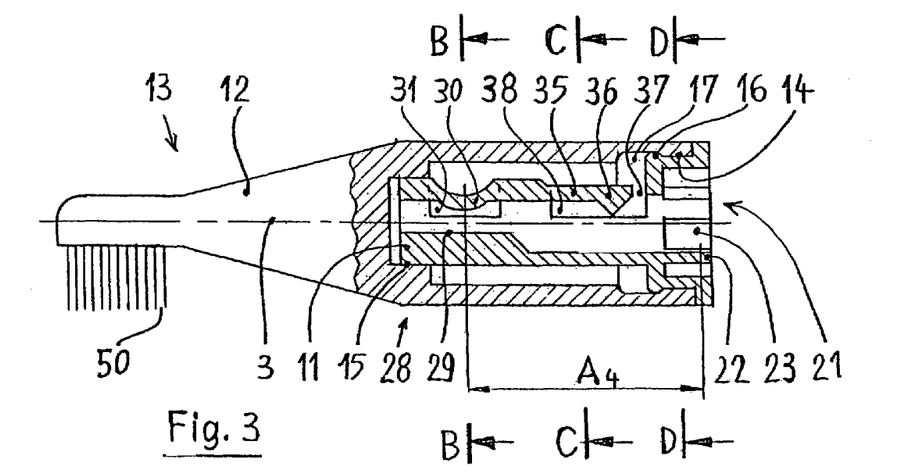
FIG. 3 is a view of a brush attachment of the invention.

FIG. 1 shows a connecting area of a handle 1 of an electric toothbrush for connecting to a brush attachment 13 of the invention shown in FIG. 3.

The handle 1 is comprised of a plastic housing and all components required for operation such as an electric motor, a gear unit, batteries or storage batteries, a controller and the like. These components are in the interior of the housing and not shown.

As illustrated in FIG. 1, a shaft 2 made in particular of metal projects directly out of the handle 1 and performs a small torsional oscillation about its longitudinal axis at a high frequency of 260 Hz, approximately. In other words, the shaft 2 executes a vibratory motion when driven by an electric drive mechanism. Other vibratory motions, such as those along the shaft axis 3 or a combination thereof for example, are also possible. This vibratory motion is directly transmitted to bristles 50 of the brush attachment 13. The bristles 50 are fixedly secured to the brush attachment 13 either directly in a bristle area or by way of a replaceable bristle holder, not shown. However, the bristles 50 do not move relative to the brush attachment but only relative to the handle 1. In other words, they move together with the brush attachment 13. The vibratory motion of the bristles 50 is used for dental cleaning and dental care.

The brush attachment 13 has a brush shank 12—preferably made of plastic—in which a plug-on part 11—preferably also made of plastic—is fastened by positive and/or frictional engagement therewith, being in particular snap-locked in the brush shank 12 by detent means. Preferably, the brush shank 12 is shaped in an essentially tubular configuration and the plug-on part 11 is constructed as a sleeve. At one front face or end 21 of the brush attachment 13 or the plug-on part 11 is an approximately circular receiving opening in which the shaft 2 can be inserted.

The brush attachment 13 is thus constructed to be pluggable onto and detachable from the shaft 2 of the handle 1.

The plug-on part 11 is equipped with a first spring element 35 acting directly on the shaft 2, as shown in FIG. 3. This element is constructed as a detent element to engage with a detent notch 8 of the shaft 2 with a snap action. The first spring element has preferably a detent finger with an approximately V-shaped detent lug 36, which engages in a V-shaped detent groove 8 of the shaft 2 such that the brush attachment 13 is also axially located relative to the shaft 2, with the detent finger transmitting axial forces. The first spring element extends preferably axially in relation to the shaft 2. With its free end the detent finger adjoins a cavity 37 of the plug-on part 11, with material recesses 38 situated to the side of the detent finger.

The brush attachment 13 is equipped in addition with a second spring element 30 arranged in an axially offset position relative to the first spring element 35.

Figure 7:
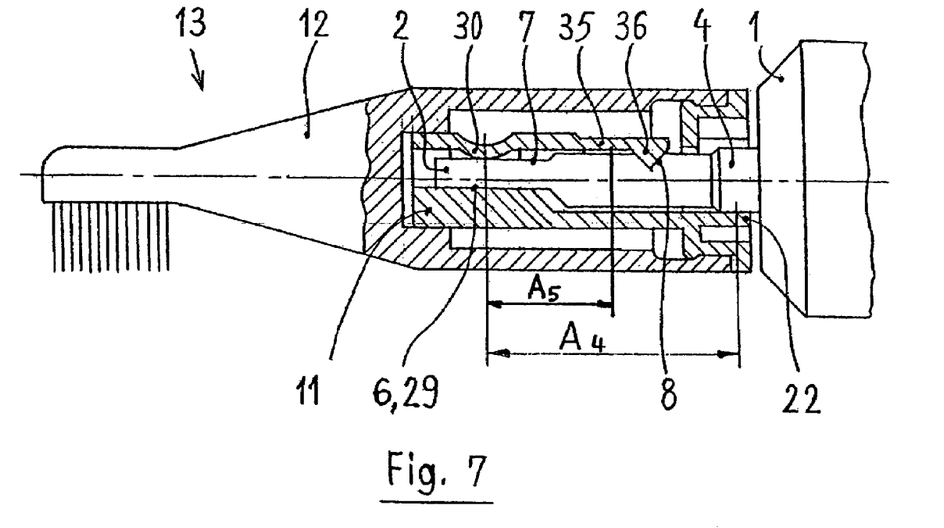
FIG. 7 is a view of a brush attachment of the invention similar to FIG. 1, but in attached condition.

According to the invention the second spring element 30 is arranged on the plug-on part 11 and acts likewise directly on the shaft 2. As the result, the brush attachment 13, or to be more precise the plug-on part 11, takes support upon two axially spaced points of the shaft 2, thus permitting the use of high drive frequencies. The axial distance $A_5$ (cf. FIG. 7)

between the first spring element 35 and the second spring element 30 amounts to preferably 5 to 20 mm, particularly around 8 to 14 mm, e.g., 12 mm, which is a good compromise between minimizing the sleeve dimensions and maximizing the noise damping.

Figure 4:
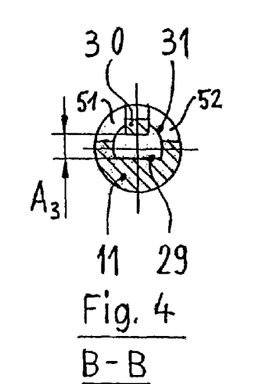
FIG. 4 is a cross-sectional view taken along the section line B-B of FIG. 3.
Figure 5:
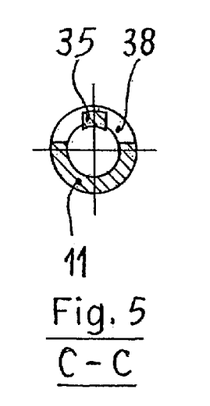
FIG. 5 is a cross-sectional view taken along the section line C-C of FIG. 3.

As FIGS. 4 and 5 show, the first spring element 35 and the second spring element 30 are arranged preferably in the same radial position, the second spring element 30 being arranged on an area close to the bristle carrier or the bristles 50 while the first spring element 35 is arranged at a location more remote from the bristle carrier, as illustrated in FIG. 3. The detent finger 35 points preferably in the direction of the handle 1.

Figure 2:
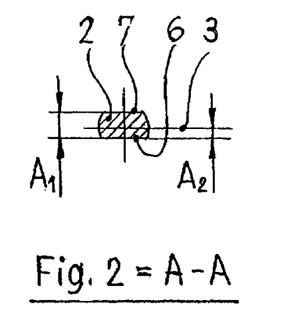
FIG. 2 is a sectional view of the shaft taken along the section line A-A of FIG. 1.

As FIGS. 3 and 7 show, the second spring element 30 is comprised of an axially aligned spring bar with a bend curved toward the shaft 2. This spring bar is constructed in particular as a bending bar. The spring bar lies between two axial slots 51, 52 or recesses 31 (FIG. 4) of the plug-on part 11. When the brush attachment 13 is plugged on, the spring bar 30 is bent slightly outwardly, its spring force operating to urge it directly against the shaft 2, as shown in FIG. 7. The detent finger 35 presses likewise with its spring bar and/or detent lug 36 against the shaft 2. The distance $A_3$ (FIG. 4) is smaller than the distance $A_1$ (FIG. 2). The difference is equal in particular to less than 1 mm.

The spring action of the bent spring bar 30 is obtained necessarily by demolding when, after the plug-on part 11 is injection-molded, a core provided in the manufacturing process for this bent shape is withdrawn.

The plug-on part 11 is equipped with a third spring element 22 in an axially offset position relative to the first two spring elements 30, 35, which lies preferably in the vicinity of the receiving opening or is arranged on the end 21 close to the handle 1. The first spring element 35 then lies between the second spring element 30 and the third spring element 22.

Figure 6:
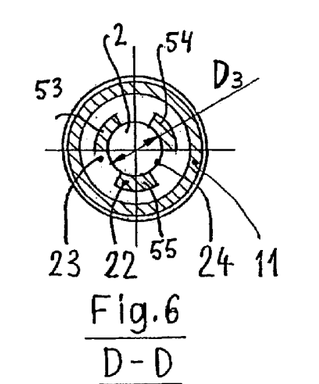
FIG. 6 is a cross-sectional view taken along the section line D-D of FIG. 3.

As becomes apparent from FIG. 6, the third spring element 22 is comprised of several, in particular three, radially offset resilient fingers 53-55, which in the mounted state also urge against the shaft 2. The fingers 53-55 extend axially and point preferably toward the handle 1 and are relatively short, preferably only 1 to 3 mm long. Free spaces 23 exist between the fingers 53-55.

In the non-inserted state the free ends of the fingers 53 to 55 adjoin an imaginary circular line 24 (FIG. 6) with a diameter $D_3$. The diameter $D_1$ of the shaft 2 in this area is bigger than the diameter $D_3$, thus producing a radial bias between a rear section 4 (FIG. 1) of the shaft 2 and the fingers 53-55 of the plug-on part 11.

As is shown in FIGS. 1 and 2, the shaft 2 is constructed with several cross sectional areas, including one area with a circular cross section and a diameter $D_1$ in the vicinity of the handle 1 for the third spring element 22, one area, which is roughly in the middle of the shaft 2, with a likewise circular cross section and a somewhat smaller diameter $D_2$ for the first spring element 35, and one forward area with a reduced cross section (cf. A1 in FIG. 2) for the second spring element 30 on the free end of the shaft 2. On this forward end close to the bristle carrier the shaft 2 has an essentially D-shaped cross section. In this region are two parallel surface areas 6 and 7. The surface area 7, which makes contact with the second spring element 30, is smaller, for example ¼ to ¾, in particular approximately half the size of the opposite surface area 6. The surface area 6 lies in the vicinity of the axis 3, while the flattening 7 or surface area 7 lies close to the circumference of a forward section 5. The distance $A_2$ can be smaller than 1 mm, for example. The surface area 6 can also meet exactly with the axis 3 or even be arranged above it. The distance $A_1$ between the two surface areas equals preferably about 1.5 to 2.5 mm or approximately half the diameter $D_2$. The diameter $D_2$ equals preferably 80% to 97% of the diameter $D_1$ and in particular 3 mm to 5 mm, for example 4 mm. The distance $A_4$ between the second and the third spring element 30, 22 is relatively large and equals preferably 20-40 mm, particularly 23-27 mm. This is favorable for the transmission of bending moments between the shaft 2 and the plug-on part 11.

The third spring element 22 lies in the shaft area with the biggest diameter $D_1$. The first spring element 35 lies in the area with the reduced diameter $D_2$, and the second spring element 30 thus lies in the D-shaped forward area of the shaft. The plug-on part 11 encloses the D-shaped area such that the brush attachment 13 can be plugged onto the shaft 2 in a certain radial position only.

A plane area 29 (FIG. 4) of the plug-on part 11 rests flush on the surface area 6 (FIG. 2) such that high torques can be transmitted. The spring bar 30 can transmit lateral forces and bending moments between the shaft 2 and the plug-on part 11.

A frontal insertion bevel 60 in the vicinity of the surface area 6 and a further insertion bevel 61 in the area of the diameter $D_2$ facilitate the plugging on such that the brush attachment 13 rotates into the correct position on its own.

FIG. 3 shows further that the plug-on part or the sleeve 11 is press-fitted into the brush shank or secured therein by frictional engagement, namely at points 14 and 15 at the ends respectively of the sleeve 11. In axial direction the sleeve 11 is additionally fastened by positive engagement of an annular, outwardly extending fastening collar 16 with the brush shank 12, for which a groove 17 is provided on the brush shank 12. The sleeve 11 is thus held by in the brush shank 12 by both frictional and positive engagement therewith.

Figure 8:
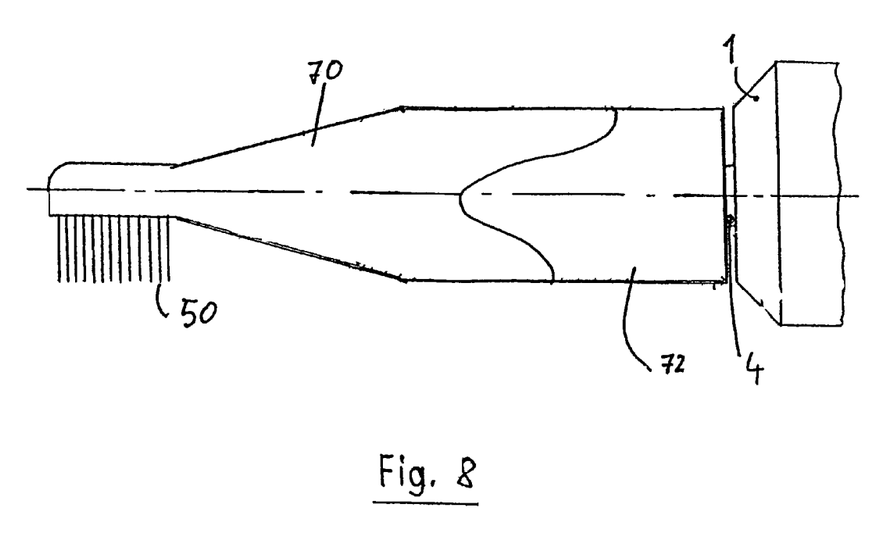
FIG. 8 is a view of a first variant of the brush attachment of the invention, showing a partial soft-elastic padding.
Figure 9:
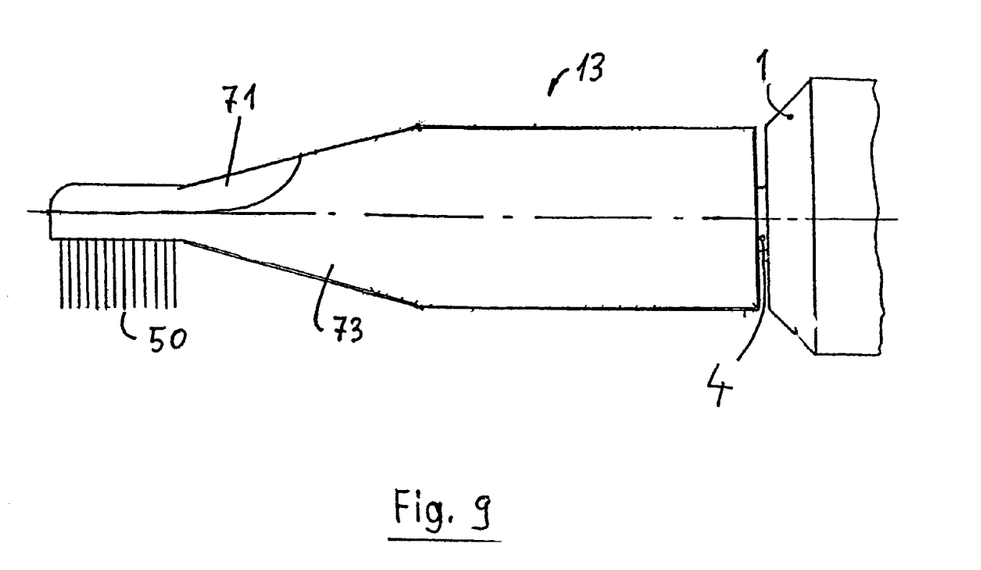
FIG. 9 is a view of a second variant of the brush attachment of the invention, showing a partial soft-elastic padding.

FIGS. 8 and 9 illustrate a very advantageous embodiment of the brush attachment 13 with soft-elastic areas. The soft-elastic construction is useful in combination with the spring element arrangement of the invention. This construction, which is shown in FIG. 8 or 9, can also be used in combination with a different plug-on solution.

The brush attachment 13 or the brush shank 12 has a soft-elastic padding 70, 71 or 76. This padding extends at least over a section of the brush attachment and covers preferably at least a rear side of the area set with bristles. In other words, this padding 70 or 71 is arranged preferably in a region proximate the bristles. A soft-elastic component, which forms the padding 70 or 71, encompasses a hard part 72 or 73, which lies in an area opposite the bristles 50. The padding 71 extends preferably over a partial area, preferably about half of a circumference, and exists only in the vicinity of the bristles 50.

The soft-elastic component can cover in addition side areas of the brush attachment in full or in part, as shown in FIG. 8.

Figure 10:
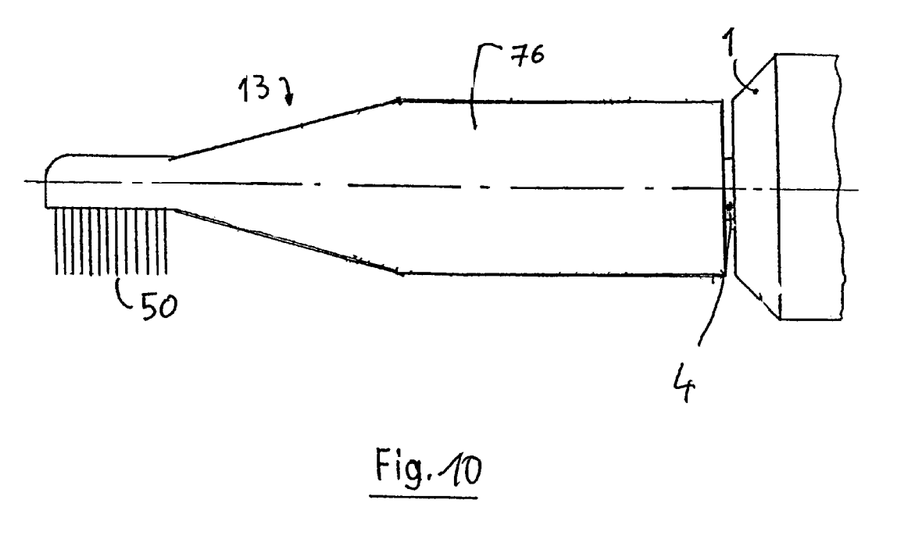
FIG. 10 is a view of another variant of the brush attachment of the invention, showing a complete soft-elastic padding.

As illustrated in FIG. 10, a soft-elastic padding 76 can also enclose the brush attachment 13 in full.

The soft-elastic, in particular rubbery plastic mass is injection-molded using a two-component plastic injection-molding process.

This elastic padding can have a structured, in particular studded or ribbed, surface, such that the brush shank is particularly good to grip.

If the bristles 50 are omitted or replaced by massage elements, such a vibrating device with a soft-elastic component can also be used as a massaging device.

A number of embodiments have been described. Nevertheless, it will be understood that various modifications may be made without departing from the spirit and scope of the invention. Accordingly, other embodiments are within the scope of the following claims. The foregoing embodiments are therefore to be considered in all respects illustrative rather than limiting of the invention described herein. The scope of the invention is thus indicated by the appended claims rather than by the foregoing description, and all changes which come within the meaning and range of equivalency of the claims are therefore intended to be embraced herein.

LIST OF REFERENCE CHARACTERS 1 handle
2 shaft
3 axis
4 section
5 section
6, 7 surface areas
8 detent groove
11 plug-on part
12 brush shank
13 brush attachment
14, 15 points
16 fastening collar
17 groove
21 end
22 third spring element
23 free spaces
24 circular line
30 second spring element
35 first spring element
36 detent lug
37 cavity
38 material recesses
50 bristles
51, 52 slots
53-55 fingers
61, 62 insertion bevels
70, 71, 76 padding
72, 73 hard part

What is claimed is:

1. A brush attachment adapted to be attached to and detached from a drivable shaft of a handle of an electric toothbrush, the attachment comprising:
    a bristle area comprising bristles;
    a brush shank; and
    a plug-on part disposed in the brush shank, the plug-on part comprising a first spring element and a second spring element,
    wherein both the first spring element and the second spring element are configured to act directly on a drivable shaft of a handle of an electric toothbrush when the brush attachment is plugged onto a drivable shaft of a handle of an electric toothbrush,
    wherein the first spring element and the second spring element are arranged in an axially offset relation to each other; and
    wherein the second spring element is arranged on an area proximate the bristles while the first spring element is arranged at a location more remote from the bristles.

2. The brush attachment as claimed in claim 1, wherein said first and said second spring elements are arranged in substantially the same radial position.

3. The brush attachment as claimed in claim 1, wherein said first spring element comprises a detent finger that extends axially and that is configured to engage an approximately V-shaped detent groove.

4. The brush attachment as claimed in claim 3, wherein said detent finger is configured to point in a direction of a handle of an electric toothbrush when the brush attachment is plugged onto a drivable shaft of a handle of an electric toothbrush.

5. The brush attachment as claimed in claim 1, wherein said second spring element comprises an axially aligned spring bar with a bend curved in a direction of a drivable shaft of a handle of an electric toothbrush when the brush attachment is plugged onto a drivable shaft of a handle of an electric toothbrush, whereby said spring bar is arranged between two axial slots of the plug-on part.

6. The brush attachment as claimed in claim 1, wherein said plug-on part further comprises a third spring element arranged in an axially offset position relative to the first two spring elements.

7. The brush attachment as claimed in claim 6, wherein said first spring element is disposed between the second and the third spring element, with the third spring element being configured to be arranged on an area proximate a handle of an electric toothbrush when the brush attachment is plugged onto a drivable shaft of a handle of an electric toothbrush.

8. The brush attachment as claimed in claim 6, wherein said third spring element further comprises radially offset resilient fingers that are configured to urge against a drivable shaft of a handle of an electric toothbrush when the brush attachment is plugged onto a drivable shaft of a handle of an electric toothbrush.

9. The brush attachment as claimed in claim 6, wherein said plug-on part is configured to be fitted onto a shaft comprising two circular cross sectional areas of various diameters, with different ones of the spring elements each resting against a corresponding one of the different cross sectional areas.

10. The brush attachment as claimed in claim 9, wherein said plug-on part comprises a first diameter for the first spring element and a second, bigger diameter for the third spring element.

11. The brush attachment as claimed in claim 1, wherein said plug-on part is releasably attached to the brush shank by frictional engagement therewith.

12. The brush attachment as claimed in claim 1, wherein said plug-on part is releasably attached to the brush shank by a snap-lock connection.

13. The brush attachment as claimed in claim 1, wherein said plug-on part is releasably attached to the brush shank by a press-fit connection.

14. The brush attachment as claimed in claim 1, further comprising a soft elastic padding extending at least over a section of the brush attachment and arranged in a region proximate the bristles.

15. The brush attachment as claimed in claim 14, wherein said soft elastic padding extends along a rear side of the bristle area, opposite the bristles.

16. The brush attachment as claimed in claim 15, wherein said soft elastic padding extending along a rear side of the bristle area comprises a soft-elastic, rubbery plastic component substantially encompassing a hard part of plastic.

17. The brush attachment as claimed in claim 14, wherein said padding extends over substantially half of a circumference of the brush attachment.

18. The brush attachment as claimed in claim 17, wherein said padding extends proximate the bristles.

19. The brush attachment as claimed in claim 14, wherein a soft elastic component substantially covers lateral regions of the brush attachment.

20. The brush attachment as claimed in claims 14, wherein said soft elastic padding comprises a studded, lugged or ribbed surface.

21. The brush attachment as claimed in claim 1, wherein the bristles are directly secured to the brush attachment.

22. The brush attachment as claimed in claim 1, wherein the bristles are fixedly secured to the brush attachment with a detachable connecting element.

23. The brush attachment as claimed in claim 1, wherein said brush shank is shaped in a substantially tubular configuration and said plug-on part is constructed as a sleeve.

24. A hand-held electric toothbrush comprising;
a handle comprising a drivable shaft; and
a brush attachment adapted to be attached to and detached from the drivable shaft of the handle, the brush attachment comprising:
a bristle area comprising bristles,
a brush shank, and
a plug-on part disposed in the brush shank, the plug-on part comprising a first spring element and a second spring element,
wherein both the first spring element and the second spring element are configured to act directly on the drivable shaft when the brush attachment is plugged onto the handle,
wherein the first spring element and the second spring element are arranged in an axially offset relation to each other, and
wherein the second spring element is arranged on an area proximate the bristles while the first spring element is arranged at a location more remote from the bristles.

25. The hand-held electric toothbrush as claimed in claim 24, wherein said drivable shaft has a substantially D-shaped cross section at its forward end close to the bristles and a circular cross section at its rear end proximate the handle, the forward end of the drivable shaft preferably having a flattening against which the second spring element rests.

26. The hand-held electric toothbrush as claimed in claim 24, wherein said drivable shaft projects directly out of said handle.

27. The hand-held electric toothbrush as claimed in claim 24, wherein said brush attachment executes a high-frequency vibratory motion greater than about 100 Hz.

28. The hand-held electric toothbrush as claimed in claim 24, wherein said brush attachment executes a high-frequency vibratory motion between about 200 Hz and 500 Hz.

29. The hand-held electric toothbrush as claimed in claim 24, wherein said brush attachment executes a high-frequency vibratory motion at about 260 Hz.

30. A brush attachment adapted to be attached to and detached from a drivable shaft of a handle of an electric toothbrush, the attachment comprising:
a bristle area comprising bristles;
a brush shank; and
a plug-on part disposed in the brush shank, the plug-on part comprising a first spring element and a second spring element, wherein both the first spring element and the second spring element are configured to act directly on a drivable shaft of a handle of an electric toothbrush when the brush attachment is fitted onto a drivable shaft of a handle of an electric toothbrush,
wherein the first spring element and the second spring element are arranged in an axially offset relation to each other,
wherein the second spring element is arranged on an area proximate the bristles while the first spring element is arranged at a location more remote from the bristles, and
wherein said second spring element comprises an axially aligned spring bar with an arcuate portion having a convex side that extends toward a drivable shaft of a handle of an electric toothbrush when the brush attachment is fitted onto a drivable shaft of a handle of an electric toothbrush, whereby said spring bar is arranged between two axial slots of the plug-on part.

31. The brush attachment as claimed in claim 30, wherein said first and said second spring elements are arranged in substantially the same radial position.

32. The brush attachment as claimed in claim 30, wherein said first spring element comprises a detent finger that extends axially and that is configured to engage an approximately V-shaped detent groove.

33. The brush attachment as claimed in claim 32, wherein said detent finger extends radially inward.

34. The brush attachment as claimed in claim 32, wherein said second spring element comprises an axially aligned spring bar with a bend curved in a direction of a drivable shaft of a handle of an electric toothbrush when the brush attachment is fitted onto a drivable shaft of a handle of an electric toothbrush, whereby said spring bar is arranged between two axial slots of the plug-on part.

35. The brush attachment as claimed in claim 32, wherein said plug-on part further comprises a third spring element arranged in an axially offset position relative to the first and second spring elements.

36. The brush attachment as claimed in claim 32, wherein said first spring element is disposed between the second and the third spring element, with the third spring element being configured to be arranged on an area proximate a handle of an electric toothbrush when the brush attachment is plugged onto a drivable shaft of a handle of an electric toothbrush.

37. A hand-held electric toothbrush comprising:
a handle comprising a drivable shaft; and
a brush attachment adapted to be attached to and detached from the drivable shaft of the handle, the attachment comprising:
a bristle area comprising bristles;
a brush shank; and
a plug-on part disposed in the brush shank, the plug-on part comprising a first spring element and a second spring element,
wherein both the first spring element and the second spring element are configured to act directly on the drivable shaft of the handle of the electric toothbrush when the brush attachment is fitted onto the shaft of the handle of the electric toothbrush,
wherein the first spring element and the second spring element are arranged in an axially offset relation to each other,
wherein that second spring element is arranged on an area proximate the bristles while the first spring element is arranged at a location more remote from the bristles, and
wherein said second spring element comprises an axially aligned spring bar with an arcuate portion having a convex side extending toward the shaft, whereby said spring bar is arranged between two axial slots of the plug-on part.

38. The hand-held electric toothbrush as claimed in claim 37, wherein said shaft has a substantially D-shaped cross section at its forward end close to the bristle carrier region and a circular cross section at its rear end proximate the handle, the forward end of the shaft preferably having a planar region configured to engage the second spring element.

39. A replaceable brush head for a powered toothbrush handle having a drive shaft extending axially and protruding from the handle, the brush head comprising:
a housing defining a bristle carrier region carrying at least one bristle tuft, said housing having a bore defining an inner surface that bounds an inner longitudinal cavity configured for receiving a drive shaft of a powered toothbrush handle;

a first spring element disposed within the head and located at a first axial position, the first spring comprising a detent that extends radially inward; and a second spring element disposed within the head and spatially removed from the first spring, the second spring oriented in a substantially similar radial position as the first spring, wherein both the first spring element and the second spring element are configured to act directly on a drive shaft of a powered toothbrush handle when the brush head is plugged onto a drive shaft of a powered toothbrush handle, and wherein the first spring element and the second spring element are arranged in an axially offset relation to each other and wherein the second spring element is arranged on an area proximate the bristle carrier region while the first spring element is arranged at a location more remote from the bristle carrier region.

40. The replaceable brush head as claimed in claim 39, wherein said first and said second spring elements are arranged in substantially the same radial position.

41. The replaceable brush head as claimed in claim 39, wherein said detent finger extends axially and is configured to engage an approximately V-shaped detent groove.

42. The replaceable brush head as claimed in claim 39, wherein said second spring element comprises an axially aligned spring bar with a bend curved in the direction of a drive shaft of a powered toothbrush handle when the replaceable brush head is plugged onto a drive shaft of a handle of an electric toothbrush, whereby said spring bar is arranged between two axial slots of the housing.

43. The replaceable brush head as claimed in claim 39, wherein said housing is configured to releasably attach to a powered toothbrush handle by frictional engagement therewith.

44. The replaceable brush head as claimed in claim 39, wherein said housing is configured to releasably attach to a powered toothbrush handle by a snap-lock connection.

45. The replaceable brush head as claimed in claim 39, wherein said housing is configured to releasably attach to a powered toothbrush handle by a press-fit connection.

46. A replaceable brush head for a powered toothbrush handle having a drive shaft protruding from the handle, comprising:

a housing defining a bristle carrier region carrying one or more bristle tufts, said housing having a bore defining an inner surface that bounds a longitudinal cavity for receiving a drive shaft of a powered toothbrush handle; and first, second and third springs located on the head at respective different first, second and third axial positions, wherein the second spring is arranged on an area proximate the bristle carrier region while the first spring is arranged at a location more remote from the bristle carrier region.

47. The replaceable brush head as claimed in claim 46, wherein said first spring is disposed between the second and the third spring.

48. The replaceable brush head as claimed in claim 47, wherein the first and third springs are disposed at substantially equal distances away from the second spring.

49. The replaceable brush head as claimed in claim 46, wherein said third spring is disposed within the housing bore.

50. The replaceable brush head as claimed in claim 46, wherein said third spring further comprises radially offset resilient fingers.

51. The replaceable brush head as claimed in claim 46, wherein said housing is configured to be fitted onto a shaft comprising two circular cross sectional areas of various diameters, with different springs resting against the different cross sectional areas.

52. The replaceable brush head as claimed in claim 46, wherein said housing comprises a first diameter for the first spring and a second, larger diameter for the third spring.

* * * * *